United States Patent [19]

Bolcsak et al.

[11] Patent Number: 5,100,662
[45] Date of Patent: Mar. 31, 1992

[54] STEROIDAL LIPOSOMES EXHIBITING ENHANCED STABILITY

[75] Inventors: Lois E. Bolcsak, Lawrenceville; Lawrence Boni, Monmouth Junction; Mircea C. Popescu, Plainsboro; Paul A. Tremblay, Hamilton, all of N.J.

[73] Assignee: The Liposome Company, Inc., Princeton, N.J.

[21] Appl. No.: 422,047

[22] Filed: Oct. 16, 1989

Related U.S. Application Data

[63] Continuation-in-part of Ser. No. 397,777, Aug. 23, 1989, abandoned, which is a continuation-in-part of Ser. No. 236,702, Aug. 25, 1988, abandoned, and a continuation-in-part of Ser. No. 236,701, Aug. 25, 1988, abandoned.

[51] Int. Cl.$^5$ ............. A61K 9/127; A61K 9/133; A61K 39/39; A61K 39/385
[52] U.S. Cl. ................... 424/88; 424/89; 424/92; 424/450; 428/402.2
[58] Field of Search ............ 428/402.2; 424/450, 424/88, 89, 92

[56] References Cited

U.S. PATENT DOCUMENTS

| | | | |
|---|---|---|---|
| 3,859,047 | 1/1975 | Klein | 23/230 |
| 4,040,784 | 8/1977 | Deshmukh | 23/230 |
| 4,042,330 | 8/1977 | Deshmukh | 23/230 |
| 4,053,585 | 10/1977 | Allison et al. | 424/498 X |
| 4,148,876 | 4/1979 | Almeida et al. | 424/89 |
| 4,183,847 | 1/1980 | Deshmukh | 260/112 |
| 4,189,400 | 2/1980 | Prekach et al. | 252/408 |
| 4,224,179 | 9/1980 | Schneider | 252/316 |
| 4,372,949 | 2/1983 | Kodama et al. | 424/450 X |
| 4,393,044 | 7/1983 | Takaishi | 424/63 |
| 4,396,630 | 8/1983 | Riedl et al. | 424/88 X |
| 4,522,803 | 6/1985 | Lenk et al. | 424/1.1 |
| 4,588,578 | 5/1986 | Fountain et al. | 424/1.1 |
| 4,693,999 | 9/1987 | Axellson et al. | 514/174 |
| 4,721,612 | 1/1988 | Janoff et al. | 424/1.1 |
| 4,826,687 | 5/1989 | Nerome et al. | 264/4.6 X |
| 4,880,634 | 11/1989 | Speiser | 424/450 |
| 4,915,951 | 4/1990 | Baldeschwieler et al. | 424/450 |
| 4,931,361 | 6/1990 | Baldeschwieler et al. | 428/402.2 |
| 4,971,803 | 11/1990 | Li et al. | 424/450 |

FOREIGN PATENT DOCUMENTS

| | | | |
|---|---|---|---|
| 0028456 | 5/1981 | European Pat. Off. | |
| 8300294 | 2/1983 | World Int. Prop. O. | 424/450 |
| WO87/00238 | 1/1986 | World Int. Prop. O. | 424/450 |
| WO87/00043 | 1/1987 | World Int. Prop. O. | 424/450 |

OTHER PUBLICATIONS

Bangham et al., "Diffusion of Univalent Ions Across the Lamellae of Swollen Phospholipids", 1965, J. Mol. Biol. 13:238-252.
Benz et al., "Destabilization of Phosphatidylethanolamine-Containing Liposomes: Hexagonal Phase and Asymmetric Membranes", 1987, Biochem. 26:2105-2116.
Brockerhoff et al., "Preparation and Structural Studies of Cholesterol Bilayers", 1982, Biochim. Biophys. Acta. 691:227-232.
Davis et al., "Liposomes As Adjuvants with Immunopurified Tetanus Toxoid: The Immune Response", 1986/87, Immunol. Let. 14:341-348.
Ellens et al., "Effect of H+ on the Stability and $Ca^{2+}$-Induced Fusion of Liposomes Containing Acidic Lipids", 1984, Biophys. J. vol. 45:M-Pos54.
Gregoriadis et al., "Liposomes As Immunological Adjuvants: Antigen Incorporation Studies", 1987, Vaccine 5:145-151.
Gregoriadis et al., "Liposomes As Adjuvants With Immunopurified Tetanus Toxoid: Influence of Liposomal Characteristics", 1987, Immuno. 61:229-234.
Kramp et al., "Liposomal Enhancement of the Immunogenicity of Adenovirus Type 5 Hexon and Fiber Vaccines", 1979, Infec. and Immun. 25(2):771-773.
Papahadjapoulos et al., "Phospholipid Model Membranes I. Structural Characteristics of Hydrated Liquid Crystals," 1967, Biochim. Biophys. Acta, 135:624-638.
Schrader, "Use of Phytosterols in Cosmetic Products", D&CI/Sep. 1983, p. 34 and Oct. 1983, p. 46.
Shinitzky et al., "Effective Tumor Immunization Induced by Cells of Elevated Membrane-Lipid Microviscosity", 1979, Proc. Natl. Acad. Sci. 76(10):5313-5316.
Tilcock, Chemistry and Physics of Lipids, 40 (1986) 109-125.
Spanjer, H. et al., Biochim. Biophys. Acta. vol. 816 (1985), pp. 396-402.
Davis et al., Immunology Letters, vol. 14, pp. 230, 232, (1986/1987).
Alving, C., Vaccine, vol. 4, pp. 166, 167 (1986).

Primary Examiner—Richard D. Lovering
Assistant Examiner—John M. Covert
Attorney, Agent, or Firm—Allen Bloom; Ronald G. Ort

[57] ABSTRACT

The present invention relates to novel liposomes and liposome-like structures (vesicles) comprising an amount of a derivatized sterol either alone or in combination with additional liposome-forming lipids.

Sterols such as cholesterol or other lipids, to which numerous charged or neutral groups are attached, may be used to prepare liposomes and liposome-like structures such as micelles, reverse micelles and hexagonal phases, suspensions of multilamellar vesicles or small unilamellar vesicles. The novel liposomes of the present invention may be prepared with or without the use of organic solvents. These vesicles may entrap compounds varying in polarity and solubility in water and other solvents. The vesicles of the present invention may function as vaccines after entrapment or association of an immunogen, as adjuvants, either alone or in combination with additional adjuvants, including, for example, Freund's adjuvant (and other oil emulsions), Bortedella Pertussis, aluminum salts and other metal salts and Mycobacterial products (including muramyldipeptides), among others. The present invention relates to novel liposomes and liposome-like structures (vesicles) comprising an amount of a derivatized sterol either alone or in combination with additional liposome-forming lipids.

31 Claims, No Drawings

STEROIDAL LIPOSOMES EXHIBITING ENHANCED STABILITY

This application is a continuation-in-part of U.S. patent application Ser. No. 397,777, entitled "Influenza Vaccine and Novel Adjuvants", filed Aug. 23, 1989, now abandoned which is a a continuation-in-part of U.S. patent application Ser. No. 236,702, entitled "Vaccine Steroidal Adjuvant", filed Aug. 25, 1988, now abandoned, and a continuation-in-part of U.S. patent application Ser. No. 236,701, entitled "DMPC/Cholesterol Adjuvant, filed Aug. 25, 1988, now abandoned.

FIELD OF THE INVENTION

The present invention relates to novel liposomes and liposome-like structures (vesicles) comprising an amount of a derivatized sterol either alone or in combination with additional liposome-forming lipids.

Sterols such as cholesterol or other lipids, to which numerous charged or neutral groups are attached, may be used to prepare liposomes and liposome-like structures such as micelles, reverse micelles and hexagonal phases, suspensions of multilamellar vesicles or unilamellar vesicles. The novel liposomes of the present invention may be prepared with or without the use of organic solvents. These vesicles may entrap compounds varying in polarity and solubility in water and other solvents. The vesicles of the present invention may function as vaccines after entrapment or association of an immunogen, as adjuvants, either alone or in combination with additional adjuvants, including, for example, Freund's adjuvant (and other oil emulsions), Bortedella Pertussis, aluminum salts and other metal salts and Mycobacterial products (including muramyldipeptides), among others.

BACKGROUND OF THE INVENTION

Liposomes are completely closed lipid bilayer membranes which contain entrapped aqueous volume. Liposomes are vesicles which may be unilamellar (single membrane) or multilamellar (onion-like structures characterized by multiple membrane bilayers, each separated from the next by an aqueous layer). The bilayer is composed of two lipid monolayers having a hydrophobic "tail" region and a hydrophilic "head" region. In the membrane bilayer, the hydrophobic (nonpolar) "tails" of the lipid monolayers orient toward the center of the bilayer, whereas the hydrophilic (polar) "heads" orient toward the aqueous phase. The basic structure of liposomes may be made by a variety of techniques known in the art.

The original liposome preparation of Bangham, et al. (J. Mol. Biol., 1965, 13:238-252) involves suspending phospholipids in an organic solvent which is then evaporated to dryness leaving a phospholipid film on the reaction vessel. Next, an appropriate amount of aqueous phase is added, the mixture is allowed to "swell" and the resulting liposomes which consist of multilamellar vesicles (MLVs) are dispersed by mechanical means. This technique provides the basis for the development of the sonicated unilamellar vesicles described by Papahadjopoulos et al. (Biochim. Biophys. Acta., 1968, 135:624-638), and large unilamellar vesicles. Small unilamellar vesicles have a diameter of about 100 nm or less.

Unilamellar vesicles may be produced using an extrusion apparatus by a method described in Cullis et al., PCT Application No. WO 86/,00238, published Jan. 16, 1986, entitled "Extrusion Technique for Producing Unilamellar Vesicles" incorporated herein by reference. Vesicles made by this technique, called LUVETS, are extruded under pressure once or a number of times through a membrane filter. LUVETs will be understood to be included in the term "unilamellar vesicle".

Another class of multilamellar liposomes are those characterized as having substantially equal lamellar solute distribution. This class of liposomes is denominated as stable plurilamellar vesicles (SPLV) as defined in U.S. Pat. No. 4,522,803 to Lenk, et al., monophasic vesicles as described in U.S. Pat. No. 4,588,578 to Fountain, et al. and frozen and thawed multilamellar vesicles (FATMLV) wherein the vesicles are exposed to at least one freeze and thaw cycle. The FATMLV procedure is described in Bally et al., PCT Publication No. 87/00043, Jan. 15, 1987, entitled "Multilamellar Liposomes Having Improved Trapping Efficiencies", corresponding to U.S. Pat. No. 4,975,282, issued Dec. 4, 1990. U.S. Pat. No. 4,721,612to Janoff et al. describes steroidal liposomes for a variety of uses. The teachings of these references as to preparation and use of liposomes are incorporated herein by reference.

In the vaccine art immunogens are introduced into an organism in a manner so as to stimulate an immune response in the host organism. The induction of an immune response depends on many factors among which are believed to include the chemical composition and configuration of the immunogen, the immunogenic constitution of the challenged organism, and the manner and period of administration of the immunogen. An immune response has many facets, some of which are exhibited by the cells of the immune system, (e.g.,B-lymphocytes, T-lymphocytes, macrophages, and plasma cells). Immune system cells may participate in the immune response through interaction with immunogen, interaction with other cells of the immune system, the release of cytokines and reactivity to those cytokines. Immune response is conveniently (but arbitrarily) divided into two main categories—humoral and cell-mediated. The humoral component of the immune response includes production of immunoglobulins specific for the immunogen. The cell-mediated component includes the generation of delayed-type hypersensitivity and cytotoxic effector cells against the immunogen.

In some instances immune response is the result of an initial or priming dose of an immunogen that is followed by one or more booster exposures to the immunogen. Priming with relatively strong immunogens and liposomes is discussed in "Liposomal Enhancement of the Immunogenicity of Adenovirus Type 5 Hexon and Fiber Vaccines", Kramp, W. J. et al., Infection and Immunity, 25:771-773 (1979) and "Liposomes as Adjuvants with Immunopurified Tetanus Toxoid: the Immune Response", Davis, D. et al., Immunology Letters, 14:341-8 (1986/1987).

Ideally, an immunogen will exhibit two properties, the capacity to stimulate the formation of the corresponding antibodies and the propensity to react specifically with these antibodies. Immunogens bear one or more epitopes which are the smallest part of an immunogen recognizable by the combining site of an antibody or immungloublin. In particular instances immunogens or fractions of immunogens or with particular presenting conditions the immune response precipitated by the desired immunogen is inadequate or nonexistent and insufficient immunity is produced. This is particularly the case with peptide or other small molecules used as immunogens.

In such cases the vaccine art recognizes the use of substances called adjuvants to potentiate an immune response when used in conjunction with an immunogen. Adjuvants are further used to elicit immune response sooner, or a greater response, or with less immunogen or to increase production of certain antibody subclasses that afford immunological protection, or to enhance components of the immune response (e.g., humoral, cellular).

Well known adjuvants are Freund's Adjuvants (and other oil emulsions), Bortedella Pertussis, aluminum salts (and other metal salts), Mycobacterial products (including muramyl dipeptides), and liposomes. As used herein the term "adjuvant" will be understood to mean a substance or material administered together or in conjunction with an immunogen which increases the immune response to that immunogen. Adjuvants may be in a number of forms including emulsion (e.g., Freund's adjuvant) gels (aluminum hydroxide gel) and particles (liposomes) or as a solid material.

It is believed that adjuvant activity can be effected by a number of factors. Among such factors are (a) carrier effect, (b) depot formation, (c) altered lymphocyte re-circulation, (d) stimulation of T-lymphocytes, (e) direct stimulation of B-lymphocytes and (f) stimulation of macrophages.

With many adjuvants adverse reactions are seen. In some instances adverse reactions include granuloma formation at the site of injection, severe inflammation at the site of injection, pyrogenicity, adjuvant induced arthritis or other autoimmune response, or oncogenic response. Such reactions have hampered the use of adjuvants such as Freund's adjuvant.

In particular embodiments adjuvants are comprised of liposomes. U.S. Pat. No. 4,053,585 issued Oct. 17, 1977 to Allison et al. states that liposomes of a particular charge are adjuvants. Davis, D, et al., "Liposomes as Adjuvants with Immunopurified Tetanus Toxoid: Influence of Liposomal Characteristics", Immunology, 61:229-234 (1987) and; Gregoriadis, G. et al., "Liposomes as Immunological Adjuvants: Antigen Incorporation Studies", Vaccine, 5:145-151 (1987) report DMPC/cholesterol liposomes (1:1) and immunogen as giving minimally improved (over free immunogen) immunological response in unilamellar vesicles of a distinct dehydration/rehydration type with tetanus toxoid as the immunogen, a strong immunogen. In the Davis and in the Gregoriadis papers, the liposomal immunogenic response was only minimally distinguishable from the response of free immunogen. To distinguish the liposomal from free immunogen response it was necessary for the authors to dilute the tetanus toxoid to minimal response amounts.

Other substances such as immunomodulators (e.g., cytokines such as the interleukins) may be combined in adjuvants/vaccines as well. Humoral immune response may be measured by many well known methods. Single Radial Immunodifussion Assay (SRID), Enzyme Immunoassay (EIA) and Hemagglutination Inhibition Assay (HAI) are but a few of the commonly used assays of humoral immune response.

SRID utilizes a layer of a gel such as agarose containing the immunogen being tested. A well is cut in the gel and the serum being tested is placed in the well. Diffusion of the antibody out into the gel leads to the formation of a precipitin ring whose area is proportional to the concentration of the antibody in the serum being tested. EIA, also known as ELISA (Enzyme Linked Immunoassay), is used to determine total antibodies in a sample. The immunogen is adsorbed to the surface of a microtiter plate. The test serum is exposed to the plate followed by an enzyme linked immunogloublin, such as IgG. The enzyme activity adherent to the plate is quantified by any convenient means such as spectrophotometry and is proportional to the concentration of antibody directed against the immunogen present in the test sample.

HAI utilizes the capability of an immunogen such as viral proteins to agglutinate chicken red blood cells (or the like). The assay detects neutralizing antibodies, i.e. those antibodies able to inhibit hemagglutination. Dilutions of the test serum are incubated with a standard concentration of immunogen, followed by the addition of the red blood cells. The presence of neutralizing antibodies will inhibit the agglutination of the red blood cells by the immunogen.

Tests to measure cellular immune response include determination of delayed-type hypersensitivity or measuring the proliferative response of lymphocytes to target immunogen.

A variety of sterols and their water soluble derivatives have been used in cosmetics, pharmaceuticals and diagnostics. Of the water soluble sterols, for example, branched fatty acid cholesterol esters, steroid esters and PEG-phytosterols have been used in cosmetic preparations (U.S. Pat. No. 4,393,044 and European Patent Application No. 28,456; and Schrader, *Drug and Cosmetic Industry*, September, 1983, p. 33 and October 1983, p. 46). A number of water soluble cholesterols have been prepared and used as water-soluble standards for the determination of cholesterol levels in biological fluids (See, for example, U.S. Pat. Nos. 3,859,047 4,040,784; 4,042,330; 4,183,847; 4,189,400; and 4,224,229). Shinitzky et al. (1979, *Proc. Natl. Acad. Sci. USA*, 76, 5313) incubated tumor cells in tissue culture medium containing a low concentration of cholesterol and cholesteryl hemisuccinate. Incorporation of cholesterol or cholesteryl hemisuccinate into the cell membrane decreased membrane fluidity and increased membrane-lipid microviscosity.

Cholesterol and other sterols, have also been incorporated into phospholipid liposome membranes in order to alter the physical characteristics of the lipid bilayers. For example, Ellens, et al. (1984, Biophys. J. 45:70 abstract) discuss the effect of H+ on the stability of lipid vesicles composed of phosphatidylethanolamine and cholesteryl hemisuccinate. Brockerhoff and Ramsammy (1982, *Biochim. Biophys. Acta.* 691, 227) reported that bilayers can be constructed which consist entirely of cholesterol, provided that a stabilized hydrophilic anchor is provided. Multilamellar and unilamellar cholesterol liposomes have been prepared in a conventional manner. More recently, Janoff et al., U.S. Pat. No. 4,721,612, relevant portions of which are incorporated by reference herein, describe methods and compositions for the preparation of lipid vesicles, the bilayers of which comprise a salt form of an organic acid derivative of a sterol, for example, the tris-salt form of a sterol hemisuccinate. The vesicles of Janoff may entrap numerous bioactive agents including insulin, growth hormone, diazepam, indomethacin and tylosin, among others; however, most of the liposomes disclosed therein are not storage stable, i.e., capable of remaining stable for a period of at least two years under standard storage conditions.

SUMMARY OF THE INVENTION

The present invention relates to a number of liposome and liposome-like structures (vesicles) formed from derivatized sterols of the present invention. The derivatized sterols according to the present invention have the general structure:

FIGURE 1

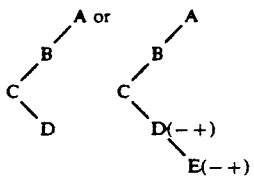

where A is a core molecule comprising a sterol, a steroid, a bile acid or an intermediate of sterol metabolism; B is a chemical bridge such as an ester, ether, sulfide (thioether), alkyl (methylene, ethylene, propylene, butylene, etc.), amide, amine, phosphonate, thioester, sulfonate or disulfide between the core molecule (A) and an anchor molecule C; C is selected from among linear, branched or cyclic structures terminating in a charged or hydrophilic group D; D, the proximal anchor, is a hydrophilic or charged group, preferably a charged group, selected from among a carboxylate, carbonate, phosphate, sulfonate, sulfate, borate, protonated amine, quaternary amine, imidazole, sulfonium, pyrrolidone, pyrrole and pyridinium; and E is a counterion to said group D when D is charged, selected from among an acetate, sulfate, sulfonate, phosphate, arsenate, borate, nitrate, chlorate, a metal ion, charged amine, including a quaternary amine, imidazole, sulfonium and diazonium salt, among others, including larger molecules, for example, amino acids, EDTA, TRIS, choline, peptides, nucleosides, nucleotides and oligo- and polynucleotides, among others.

The vesicles formed from the derivatized sterols of the present invention are generally storage stable, i.e., they can be stored for periods of at least one year and preferably for periods of at least two years without exhibiting substantial breakdown in the derivatized sterols.

The derivatized sterols of the present invention form liposomes and liposome-like structures (vesicles) which may function as adjuvants or as delivery vehicles for therapeutic and diagnostic purposes. As used throughout the specification and claims, the term "vesicle" is used to embrace all liposome and liposome-like structures which may be made with the derivatized sterols of the present invention. The vesicles of the present invention may be used to entrap numerous biologically active agents including water soluble and insoluble agents, including immunogens and adjuvants, as more fully described herein.

In one method aspect of the present invention, the method for preparing the derivatized sterol vesicles of the present invention involves adding to an aqueous buffer a salt form of a derivatized sterol capable of forming closed bilayers in an amount sufficient to form completely closed bilayers which entrap an aqueous compartment. A suspension of multilamellar vesicles may be formed by shaking the mixture. The formation of vesicles is facilitated if the aqueous buffer also contains the counterion of the salt (E) in solution. The counterion is preferably a single-charged species.

The vesicles may be used to entrap numerous bioactive agents, including immunogens and adjuvants. One particularly advantageous application of the liposomes of the present invention includes entrapping insoluble bioactive agents or agents that are only sparingly soluble in water. This advantageously allows for the administration in vivo of high concentrations of the water insoluble agents.

The vesicles of the present invention exhibit a number of distinct advantages over prior art vesicles. Some advantages include:

1). Ease and speed of formation;
2). High encapsulation efficiencies;
3). No requirement for the use of organic solvents for their preparation;
4). High utility for targetting applications;
5). pH sensitivity which allows the contents to be "dumped" at a site as a function of the pH of the site;
6). Cells endocytose these vesicles more readily than noncharged vesicles; and
7). Stability is enhanced in comparison to cholesterol hemisuccinate (CHS) vesicles.

Further embodiments of the present invention relate to an immunizing dosage form comprising a vesicle of the present invention in combination with an immunogen, for example, an influenza immunogen wherein said vesicle and immunogen are present in an immunization dose. In one embodiment the immunogen comprising the hemagglutinin fragment or the bromelain fragment of influenza is in combination with the vesicles of the present invention. In another embodiment the dosage form is a liposome such as a multilamellar vesicle, particularly those multilamellar vesicles at least about 1 micron in diameter. In certain embodiments the immunogen is entrapped in the liposome.

In preferred embodiments of the immunogen dosage form of the present invention, a given dose of the immunogen is entrapped in the liposome, preferably a multilamellar vesicle containing an adjuvant amount of the derivatized sterols according to the present invention. Preferably these vesicles are at least about 1 micron in diameter. Another useful vesicle according to the present invention comprises DMPC in combination with an adjuvant amount of a derivatized sterol according to the present invention. In certain cases, small amounts of cholesterol may be added as well. Preferred vesicles comprise DMPC/derivatized sterol in a molar ratio of from about 80:20 to about 20:80. Most preferably, the ratio of DMPC/derivatized cholesterol is about 40:60 to about 60:40 and the vesicle is a multilamellar vesicle such as an SPLV.

The vesicles of the present invention may function as vaccines after entrapment or association of an immunogen, as adjuvants, either alone or in combination with additional adjuvants, including, for example, Freund's adjuvant (and other oil emulsions), Bortedella Pertussis, aluminum salts and other metal salts and Mycobacterial products (including muramyldipeptides), among others.

The present invention relates to novel liposomes and liposome-like structures (vesicles) comprising an amount of a derivatized sterol either alone or in combination with additional liposome-forming lipids.

In specific embodiments of the present invention including immunogens, the immunogen is selected from the group comprising proteins, peptides, polysaccharides, nucleic acids, lipids, glycolipids, lipoproteins, lipopolysaccharides, synthetic peptides or bacterial fractions, viral fractions, protozal fractions, tissue fractions, or cellular fractions. Specific immunogens are influenza fractions such as hemagglutinin, parainfluenza 3 (fusion and hemagglutinin-neuraminidase), malaria sporozoite fractions, hepatitis (A, B, and non-A/non-B) fractions, meningococcus fractions, HIV fractions (all strains), and melanoma fractions.

In certain preferred embodiments of the immunization aspect of the present invention, the dosage form of the invention may further include an immunomodulator such as a cytokine.

Another aspect of the present invention includes a method of potentiating an immune response in an animal, including a human, comprising the step of administering to such animal an immunization dose of a composition comprising a derivatized sterol according to the present invention and an immunogen. In one embodiment the method for potentiating the immune response includes using a dose which includes a vesicle, for example, a multilamellar vesicle. Preferred multilamellar vesicles are at least about 1 micron in diameter. In certain embodiments the immunogen is entrapped in the liposome and in other embodiments the immunogen is ionically associated with the surface of the liposome containing the derivatized sterol.

In preferred embodiments of the present invention, the method of potentiating an immune response utilizes a dose that contains a derivatized sterol having a carboxylic acid as modifying moiety (D) and tris (hydroxymethyl) aminomethane as counterion (E). In these preferred embodiments, the linkage (B) is preferably an alkylene, amide, ether or thioether to promote the storage stability of the composition. In other preferred embodiments anchor molecule (C) contains from 2 to 8 carbon atoms, is a carboxylic acid-containing derivative, is a hydroxy acid derivative such as citric acid, is an amine-containing derivative including amino acid derivatives, and may include a polyamine or a polycarboxylic acid-containing compound.

In specific embodiments of the method of potentiating an immune response of this invention the immunogen is selected from the group comprising proteins, peptides, polysaccharides, nucleic acids, lipids, glycolipids, lipoproteins, lipopolysaccharides, synthetic peptides or bacterial fractions, viral fractions, protozal fractions, tissue fractions, or cellular fractions. The method of potentiating an immune response of the invention may further include using an immunomodulator such as a cytokine.

Another embodiment of the invention comprises a method of potentiating an immune response in an animal, including a human, comprising the use of an adjuvant wherein the adjuvant comprises a derivatized sterol according to the present invention.

In preferred embodiments, the method of potentiating an immune response with an adjuvant of the present invention uses a dose that includes a derivatized sterol wherein the molecule contains a tris (hydroxymethyl) aminomethane or sodium as the counterion (E). In these preferred embodiments, the linkage (B) is preferably an alkylene, amide, ether or thioether to promote the storage stability of the composition and anchor molecule (C) contains from 2 to 8 carbon atoms, is a carboxylic acid containing derivative, a hydroxy acid derivative such as citric acid, an amine containing derivative including amino acid derivatives, or a polyamine or a polycarboxylic acid containing compound.

This invention further comprises a method of priming an immune response in an animal, including a human, comprising the step of administering to the animal a priming immunization dose of a composition comprising an a liposome adjuvant—any type of liposome—and particularly a liposome which is a derivatized sterol of the present invention and an adjuvant-obligatory immunogen such that administration of a booster dose of adjuvant-obligatory immunogen absent adjuvant further potentiates immune response. The method of priming an immune response in an animal, in a particular embodiment, uses a salt form of a derivatized sterol wherein the counterion (E) is a (hydroxymethyl) aminomethane salt form and proximal anchor (D) is a carboxylic acid. Priming, using an immunogen that would not generate an immune response absent an adjuvant is particularly included in this embodiment.

In other embodiments of the method of priming an immune response in an animal the vesicle comprises a derivatized sterol wherein anchor molecule (C) contains from 2 to 8 carbon atoms, is a carboxylic acid containing derivative, a hydroxy acid derivative such as citric acid, an amine-containing derivative including amino acid derivatives, or a polyamine or a polycarboxylic acid-containing compound. A preferred embodiment of the method of priming further includes immunizing a primed animal by the step of administering to said animal at least one booster dose of adjuvant-obligatory immunogen absent adjuvant.

An additional aspect of this invention is a method of conferring immunity on an animal, including a human, comprising the step of administering to such animal a therapeutically effective immunization course at least one element of which includes administering an immunization dose of a composition comprising an immunogen and a derivatized sterol of the present invention. In one embodiment the composition further comprises a vesicle (including multilamellar vesicles) preferably wherein the immunogen is entrapped in the vesicles most preferably in liposomes at least about 1 micron in diameter. In employing this method the composition further can comprise a derivitized sterol wherein said counterion (E) is sodium or a tris (hydroxymethyl) aminomethane salt form of an organic acid derivative. In these preferred embodiments, the linkage (B) is preferably an alkylene, amide, ether or thioether to promote the storage stability of the composition. In other preferred embodiments anchor molecule (C) contains from 2 to 8 carbon atoms, is a carboxylic acid containing derivative, a hydroxy acid derivative such as citric acid, an amine containing derivative including amino acid derivatives, or a polyamine or a polycarboxylic acid containing compound.

Further, this invention includes a dosage form comprising an immunogen and a multilamellar liposome comprising DMPC in an immunization dose in combination with a derivatized sterol according to the present invention. In this aspect of the present invention, vesicles include an "adjuvant inducing amount" of the derivatized sterol. As used herein, the term "adjuvant inducing amount" is used to describe that amount of derivatized sterol which, when included in vesicles of the present invention produces an adjuvant effect. In further embodiments aluminum adjuvants such as aluminum hydroxide gel are included. In one embodiment the liposome of the dosage form comprises DMPC/cholesterol in a molar ratio of about 80:20 to about 20:80, preferably about 70:30. In specific embodiments the dosage form multilamellar liposome is an SPLV and/or at least 1 micron in diameter and particularly a SPLV containing DMPC:cholesterol in a ratio of about 70:30.

In particular embodiments of the dosage form the immunogen is selected from the group comprising proteins, peptides, polysaccharides, bacterial fractions, viral fractions, protozoal fractions, synthetic peptides or lipopolysaccharides. Furthermore the dosage form may comprise an immunomodulator including a cytokine. Additionally the dosage form may comprise a suitable pharmaceutical carrier. Another aspect of this invention includes a method of potentiating an immune response in an animal, including a human, comprising the step of administering to such animal an immunization dose of a composition comprising an immunogen and a multilamellar liposome comprising DMPC in combination with a derivitized sterol of the present invention, and optionally further including aluminum adjuvants such as aluminum hydroxide gel.

Additionally included in this invention is a method of potentiating an immune response in an animal including a human comprising the use of an adjuvant wherein the adjuvant comprises a liposome comprising DMPC in combination with an adjuvant inducing amount of a derivatized sterol of the present invention, one embodiment further including aluminum adjuvants such as aluminum hydroxide gel. In a preferred embodiment the method utilizes liposomes comprising a molar ratio of DMPC/derivatized sterol of about 80:20 to 20:80, most preferably wherein the ratio is from about 30:70 to about 70:30. In specific embodiments of the method the multilamellar liposome is an SPLV and/or at least about 1 micron in diameter and particularly a 70:30 DMPC/derivatized sterol SPLV.

In this method aspect of the present invention the immunogen is selected from among the same group of immunogens described hereinabove.

A further embodiment of the invention is a method of priming an immune response in an animal, including a human, comprising the step of administering to the animal a priming immunization dose of a composition comprising an adjuvant which is a multilamellar liposome comprising DMPC in combination with an adjuvant inducing amount of a derivatized sterol of the present invention and an adjuvant-obligatory immunogen (and optionally aluminum adjuvants such as aluminum hydroxide gel) such that administration of a booster dose of adjuvant-obligatory immunogen absent adjuvant further potentiates immune response.

The method of priming, in specific instances includes the vesicle being an SPLV multilamellar vesicle and/or the vesicle being at least about 1 micron in diameter, and preferably about 70:30 DMPC in combination with the derivatized sterol of the present invention. Specific immunogens of the dosage form and the methods include influenza fractions such as hemagglutinin, parainfluenza 3 (fusion and hemagglutinin-neuraminidase), malaria sporozoite fractions, hepatitis (A, B, and non-A/non-B) fraction, meningococcus fractions, HIV fractions (all strains), and melanoma fractions.

The invention in a further embodiment comprises a method of conferring immunity on an animal, including a human, comprising the step of administering to such animal a therapeutically effective immunization course at least one element of which is administering an immunization dose of a composition comprising an immunogen and a multilamellar liposome comprising DMPC in combination with a derivatized sterol of the present invention. In one aspect of the method the composition further comprises aluminum adjuvant such as aluminum hydroxide gel. In this method a particular liposome comprises in combination with a derivatized sterol of the present invention in an adjuvant inducing amount DMPC:derivatized sterol in a molar ratio of about 80:20 to about 20:80, preferably about 70:30 to about 30:70 and most preferably about 70:30 particularly wherein the liposome is an SPLV and including the liposome being at least about 1 micron in diameter.

In a further aspect this invention includes a dosage form comprising an immunogen and a liposome comprising DMPC in an immunization dose in combination with an adjuvant inducing amount of a derivatized sterol of the present invention. The dosage form can further include aluminum adjuvant such as aluminum hydroxide gel.

DETAILED DESCRIPTION OF THE INVENTION

The present invention is related to novel vesicles comprising an amount of a derivativized sterol either alone or in combination with at least one liposome-forming lipid. The derivatized sterols according to the present invention have the general structures:

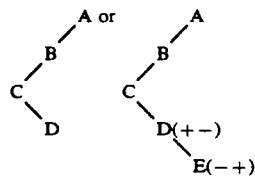

where A is a core molecule comprising a sterol, a steroid, a bile acid or an intermediate of sterol metabolism; B is a chemical bridge such as an ester, ether, sulfide (thioether), alkyl (methylene, ethylene, propylene, butylene, etc.), amide, amine, phosphonate, thioester, sulfate, sulfonate or disulfide between the core molecule (A) and an anchor molecule C; C is selected from among linear, branched or cyclic structures terminating in a charged or hydrophobic group D; D, the proximal anchor, is a hydrophilic or charged group, preferably a charged group, for example, a carbonate, phosphate, sulfonate, sulfate, borate, protonated amine, quaternary amine, imidazole, sulfonium, pyrrolidone, pyrrole or pyridinium. When D is a charged group, E is a counter-ion to said group D, for example, an acetate, sulfate, sulfonate, phosphate, arsenate, borate, nitrate, chlorate, a metal ion, charged amine, including a quaternary amine, imidazole, sulfonium or diazonium salt, among others, including larger molecules, for example, amino acids, EDTA, TRIS, choline, peptides, nucleosides, nucleotides, nucleoproteins or oligo- or polynucleotides, among others.

The derivatized sterols of the present invention form liposomes and liposome-like structures (vesicles) which may function as adjuvants or as delivery vehicles for therapeutic and diagnostic purposes. As used throughout the specification, the term "vesicle" refers to liposome bi-layer structures as well as liposome-like structures such as hexagonal phases, micelles and reverse micelles which may be formed by derivatized sterols of the present invention. The vesicles of the present invention may be used to entrap numerous biologically active agents including water soluble and insoluble agents, including immunogens and adjuvants, as more fully described herein. In certain cases where the derivatized sterols of the present invention are used to form liposomes, the derivatized sterols do not readily form the liposomes. In certain cases lipids which normally do not readily form liposomes may be added to the derivatized sterol to induce liposome formation. This is an unexpected result.

The core molecule (A of FIG. 1) may be any sterol, steroid, bile acid or intermediate of sterol metabolism which, when combined with the various components (B, C, D and E of FIG. 1) is capable of producing a vesicle. Vesicles, for purposes of the present invention, include bi-layer structures and additional structures, for example, hexagonal phases, micelles and reverse micelles which have obtained a three-dimensional structure which may be useful for entrapping bioactive agents of the present invention. Vesicles according to the present invention include micelles, reverse-micelles, hexagonal phase structures, for example $H_{II}$ phases as well as additional asymmetric membrane structures as described for example, by Bentz, et al., *Biochemistry*, 26, 2105 (1987) and C. P. S. Tilcock, "Lipid Polymorphism", *Chemistry and Physics of Lipids*, 40, 109 (1986).

Any steroid, sterol, bile acid or intermediate of steroid metabolism may be used in the present invention as the core molecule A, provided that the core molecule is capable of being derivatized in such fashion to produce a molecule A-B-C-D or A-B-C-D-E (A-B-C-D being the species when D is neutral) which is useful for forming vesicles. Generally, any steroid, sterol, bile acid or product of steroid metabolism may be used as the core molecule in the present invention, provided that the core molecule is capable of derivatization to produce the derivatized sterols of the present invention. Such sterols and steroids in general may include cholesterol, Vitamin D, phytosterols, (including but not limited to sitosterol, campesterol, stigmasterol and the like). Exemplary steroids and sterols include aldosterone, androsterone, testosterone, estrogen, ergocalciferol, ergosterol, estradiol-17alpha, estradiol-17beta, cholesterol, cholic acid, corticosterone, estriol, lanosterol, lithocholic acid, progesterone, cholecalciferol, cortisol, cortisone, cortisone acetate, cortisol acetate, deoxycorticosterone and estrone, among numerous others, with cholesterol being preferred. Exemplary bile acids include taurocholic acid, desoxycholic acid, and geicocholic acid, among others. The core molecule is chosen so that a final molecule (A-B-C-D or A-B-C-D-E) will have characteristics sufficiently amphipathic to form the vesicles of the present invention.

Core molecule A is derivatized chemically to produce a chemical link B attached to anchor molecule C. Chemical link B may be an ester, ether, alkyl (methylene, ethylene, propylene, butylene, etc.), amide, thioether, amine, phosphonate, thioester, sulfonate or disulfate linkage. Preferably, chemical link B is a group which is both acid and base stable. Chemical link B is advantageously chosen to promote the stability of liposomes during long periods of storage, preferably for periods in excess of two years. Preferred B linkages include ethers, amides and alkyl linkages.

Anchor molecule C is selected from among linear, branched-chain and cyclic structures. The anchor molecule C is selected to provide an amphipathic character to the derivatized sterol so that vesicle formation can occur. Linear structures include alkyl radicals having from 2 to 8 carbons, for example, ethyl, propyl, butyl, pentyl, hexyl, heptyl and octyl radicals. Branched chain structures include alkyl radicals of from 2 to 8 carbons in length having various alkyl side-chains. Generally, the alkyl side chains are methyl, ethyl, propyl and isopropyl groups linked to methylene groups in the alkyl chain. Cyclic structures include carbocyclic and heterocyclic ring structures including phenyl, benzyl, substituted phenyl and benzyl groups, cyclopentyl, cyclohexyl, and substituted versions of these ring structures. Heterocyclic rings include various unsubstituted and substituted tetrazoles, triazoles, pyrroles, pyrrolidines, pyrrolidones and substituted pyridines, among others. In addition, various pentose and hexose sugars, including ribose, glucose and isomers of these sugars may be incorporated into the derivatized sterols of the present invention as anchor molecule C.

The proximal end of anchor molecule C is a charged or hydrophilic group, D (proximal anchor). Group D is preferably a charged species, but may be a neutral hydrophilic species such as a hydroxyl group or other neutral hydrophilic group. A charged species is generally believed to provide sufficient amphipathic character to the derivatized sterol to promote formation of a vesicle. Group D may be negatively or positively charged. Negatively charged groups include carboxylates, carbonates, phosphates, sulfonates, borates and sulfates. Examples of positively charged groups include amines, preferably tertiary and quaternary amines, imidazoles, sulfonium groups, phosphonium groups, pyridinium groups, pyrroles, tetrazoles, and triazoles, all of which may accommodate positive charges.

We note that in certain cases when forming vesicles of the present invention group D of the derivatized sterol is in its free carboxylic acid form. During vesicle formation, however, the free carboxylic acid form will undergo salt formation in situ during liposome formation. Both the free carboxylic acid form on the derivatized sterol which undergoes salt formation to charged group D in the liposome and derivatized sterols wherein the salt formation occurs before incorporation into liposomes are contemplated by the present invention.

As indicated, group D may be charged or hydrophilic and neutral. Where D is a charged species, group E serves as a counterion to group D. The charge of the counterion is opposite that of group D. Thus, where group D is negatively charged, group E will be positively charged; conversely, where group D is positively charged, group E will be negatively charged. The group E counterion is selected based upon the ability of the group to enhance the formation of liposomes of the present invention. Preferred counterions may be positively or negatively charged. Negatively charged counterions include acetates, sulfates, phosphates, arsenates, borates, nitrates and chlorates, among other charged species. Positively charged counterions include metal ions, including potassium, sodium, lithium and magnesium, among others, charged amines including especially tertiary and quaternary amines, imidazole, pyridinium, sulfonium and phosphonium. The free base of an ionizable bioactive agent, for example, miconazole free base, among others, may also be used as the counterion.

Counterion E may be a smaller charged species or alternatively, may be a larger, more complex molecule, for example, an amino acid, peptide, peptide fragment, protein, nucleotide, nucleoside, nucleoprotein, glycoprotein, oligonucleotide, polynucleotide, ethylenediaminetetraacetic acid (EDTA), tris(hydroxymethyl)-methylamine (TRIS) and choline, among others. Counterion E is chosen to promote the ability of the derivatized sterols to form vesicles and also for its ability to complex with other molecules, for example antibodies, immunogens and other molecules which are advantageously positioned on the surface of the vesicle. Physicochemical and steric factors of counterion E may play an important role in determining the ability of the derivatized sterol to form a vesicle. Care must be chosen in selecting the counterion. However, one of ordinary skill in the art will be able to determine, through routine experimental procedures, the effect that a particular counterion has on vesicle formation and will modify the size and effect of the counterion accordingly.

The derivatized sterols of the present invention are synthesized using standard reaction sequences well known in the art. Any number of derivatives may be synthesized either by attaching a molecule E-D-C-B (or D-C-B) to core molecule A or alternatively, by building from core molecule A in step-wise fashion to produce A, then A-B, A-B-C, A-B-C-D and so on. In addition, the derivatized sterol according to the present invention may be synthesized by block synthesis, i.e., forming blocks of molecules, then coupling the molecular blocks to each other to produce a final product. For example, block A-B may be coupled to block C-D or C-D-E to produce final product A-B-C-D or A-B-C-D-E. Of course, one of ordinary skill in the art will recognize that various techniques well known in the art may be used to synthesize the derivatized sterols. This includes the use of various blocking groups to protect nucleophilic and/or electrophilic groups that would otherwise participate unfavorably in certain reactions.

The linkage (B) of anchor molecule (C) to the core molecule (A) may be via an ester, ether, amine, sulfide (thioether), alkylene, amide, amine, phosphonate, thioester, sulfate, sulfonate or disulfate. Preferably, linkage B is a storage stable linkage, for example, an ether, amine, sulfide, alkylene and amide. These linkages are synthesized by readily available methods well known in the art. The linking of anchor molecules (C) to the core molecule is generally at the reactive 3 position. The linkage of the anchor molecule to the 3 position of cholesterol is often advantageous. However, where the molecule does not contain a reactive 3 position, then a choice should be made to derivatize an alternative position which will maximize the likelihood that the resulting derivatized sterol will undergo vesicle formation.

Reaction schemes for formation of the various functional group linkages are well known in the art. For example, ether formation may proceed through use of a Williamson ether synthesis as explained in greater detail hereinbelow. Amine synthesis may proceed by simple reductive alkylation techniques well known in the synthetic chemical arts. Sulfides may be formed by nucleophilic substitution of an activated hydroxyl group, for example, a tosyl group. Alkylation of the core molecule may be performed using a wide variety of methods, including alkylation with grignard reagents. Amide formation is even more straightforward; reaction of an amine at the 3 position of the core molecule with succinic anhydride or a related anhydride results in amide formation. Other linkages may also be made by varing standard synthetic chemical methodologies.

The salt forms of the derivatized sterols can be prepared by dissolving both the organic acid or base derivative of the sterol and the counterion of the salt, e.g., the free base or acid of the salt in an appropriate volatile solvent, and removing the solvent by evaporation, lyophilization or similar technique. In other cases ion exchange may be used to produce a residue consisting of the salt form of the derivatized sterol.

Virtually any bioactive agent can be entrapped within the vesicles of the present invention. Such agents include but are not limited to antibacterial agents, antiviral agents, antifungal agents, anti-parasitic agents, tumoricidal agents, antimetabolites, polypeptides, peptides, proteins, toxins, enzymes, hormones, neurotransmitters, glycoproteins, lipoproteins, immunoglobulins, immunomodulators, vasodilators, dyes, radiolabels, radio-opaque compounds, fluorescent compounds, receptor binding molecules, anti-inflammatory agents, mydriatic compounds, local anesthetics, narcotics, vitamins, nucleic acids, polynucleotides, nucleosides, nucleotides, etc. The entrapment of two or more compounds simultaneously may be especially desirable where such compounds produce complementary or synergistic effects.

Formation of vesicles according to the present invention and entrapment of bioactive agents may be performed by following the techniques of Janoff, et al. as described in U.S. Pat. No. 4,721,612, relevant portions of which are incorporated by reference herein. The vesicles of the present invention may be formed in an organic solvent or in an aqueous buffer, with formation in an aqueous buffer preferred for vesicles which are to be administered in vivo.

The derivatized sterols of the present invention may be advantageously used in vesicles for the purpose of associating immunogens, antibodies, adjuvants and other molecules on the surface of the vesicle to promote the activity of those molecules. Vesicles according to the present invention may therefore be formed completely from the derivatized sterols of the present invention or alternatively, they may be formed from an adjuvant inducing amount of a derivatized sterol in combination with at least one other liposome-forming lipid. Vesicles may contain any amount of derivatized sterol and preferably will contain at least about 0.1 mole percent.

Any liposome-forming lipid may be used in combination with the derivatized sterols of the present invention to form vesicles. Liposome forming lipids which can be used in the vesicles of the present invention include synthetic, semisynthetic or natural phospholipids and may include phosphatidylcholine (PC), phosphatidylethanolamine (PE), phosphatidylserine (PS), phosphatidylglycerol (PG), phosphatidic acid (PA), phosphatidylinositol(PI), sphingomyelin (SPM) and cardiolipin, among others, including hydrogenated phopholipids, either alone or in combination. The phospholipids useful in the present invention may also include dimyristoylphosphatidylcholine (DMPC) and dimyristoylphosphatidylglycerol (DMPG). In other embodiments, distearoylphosphatidylcholine (DSPC), dipalmitoylphosphatidylcholine (DPPC), or hydrogenated soy phosphatidylcholine (HSPC) may also be used. Dimyristoylphosphatidylcholine (DMPC) and diarachidonoylphosphatidylcholine (DAPC) may similarly be used. Due to the elevated transition temperatures ($T_c$) of lipids such as DSPC ($T_c$ of about 65° C.), DPPC ($T_c$ of about 45° C.) and DAPC ($T_c$ of about 85° C.), such lipids are preferably heated to about their $T_c$ or temperatures slightly higher, e.g., up to about 5° C. higher than the $T_c$, in order to make these liposomes. In preferred embodiments, egg phosphatidylcholine is used.

In a number of embodiments of the present invention, a steroidal component other than the derivatized sterol of the present invention may be added to the vesicle. For purposes of the present invention any component including the above-described phospholipids and steroidal component which may be used to produce a vesicle either alone or in combination with a derivatized sterol of the present invention is termed a liposome forming lipid. Any of the above-mentioned phospholipids and derivatized sterols may be used in combination with at least one additional steroidal component selected from the group consisting of cholesterol, cholestanol, coprostanol or cholestane. In addition, polyethylene glycol derivatives of cholesterol (PEG-cholesterols), as well as the organic acid derivatives of sterols, for example cholesterol hemisuccinate (CHS) and other derivatives as disclosed in U.S. Pat. No. 4,721,612 may also be used in combination with any of the derivatized sterols of the present invention. Organic acid derivatives of alpha-tocopherol hemisuccinate, (THS) may also be used.

The vesicle entrapped agent may be administered by any suitable route, including inoculation or injection, for example, intravenous, oral, intraperitoneal, intramuscular, subcutaneous, intra-aural, intraarticular, intra-mammary, topical application, for example on the skin, scalp, ears, eyes and by absorption through epithelial or mucocutaneous linings, for example, nasal, oral, vaginal, rectal and gastrointestinal, among others.

The mode of administration may determine the sites in the organism to which the compound will be delivered. For instance, delivery to a specific site of infection may be most easily accomplished by topical application (if the infection is external, e.g., on areas such as the eyes, skin, in the ears or on afflictions such as wound or burns) or by absorption through epithelial or mucocutaneous linings (e.g., nasal, oral, vaginal, rectal, gastrointestinal, mucosa, etc.). Such topical application may be in the form of creams or ointments. The liposome containing bioactive agent may be administered alone our will generally be administered in admixture with a pharmaceutical carrier selected with regard to the intended route of administration and standard pharmaceutical practice. For parenteral administration, they are best used in the form of a sterile aqueous solution which may contain other solutes, for example, sufficient salts, glucose or dextrose to make the solution isotonic.

For the oral mode of administration, vesicles of the present invention can be used in the form of tablets, capsules, lozenges, troches, powders, syrups, elixirs, aqueous solutions and suspension, and the like. Various disintegrants such as starch, and lubricating agents may be used. For oral administration in capsule form, useful diluents are lactose and high molecular weight polyethylene glycols. When aqueous suspensions are required for oral use, certain sweetening and/or flavoring agents can be added.

The vesicles of the present invention may also be used in diagnostic assays; in this case the amount of the composition used will depend on the sensitivity of the vesicle antibody to the target components in the sample.

The present invention also relates to vesicles of the present invention further comprising an adjuvant inducing amount of a derivatized sterol of the present invention and an immunogen. Preferably, the immunogen is an influenza immunogen including the hemagglutinin fragment or the bromelain fragment. The derivatized sterols of the present invention are also useful pharmaceutical adjuvants, particularly in the form of liposomes. DMPC/cholesterol liposomes in combination with the derivatized sterols of the present invention (especially multilamellar liposomes) are also useful pharmaceutical adjuvants alone or in combination with aluminum hydroxide gels.

The various terms used to define concepts in immunology are often loosely defined or otherwise misused. For clarity, in the discussion of this invention the following definitions are used:

"Antigen" shall mean a substance or material that is recognized specifically an antibody and/or combines with an antibody.

"Adjuvant" shall mean a substance or material to potentiate an immune response when used in conjunction with an immunogen. Adjuvants are further used to elicit immune response sooner, or a greater response, or with less immunogen.

"Adjuvant inducing amount" shall mean an amount of an adjuvant effective for producing an adjuvant effect.

"Immunogen" shall mean a substance or material (including antigens) that is able to induce an immune response alone or in conjunction with an adjuvant. Both natural and synthetic substances may be immunogens. An immunogen may be a protein, peptide, polysaccharide, nucleoprotein, lipoprotein, synthetic polypeptide, or hapten linked to a protein, peptide, polysaccharide, nucleoprotein, lipoprotein or synthetic polypeptide or other bacterial, viral or protozal fractions. It will be understood that "immunogen" includes substances which do not generate an immune response (or generate only therapeutically ineffective immune response) unless associated with an adjuvant (e.g., small peptides) which will be referred to as "adjuvant-obligatory" immunogens.

"Immune response" shall mean a specific response of the immune system of an animal to antigen or immunogen. Immune response may include the production of antibodies.

"Immunization conditions" shall mean factors which affect an immune response including amount and kind of immunogen or adjuvant delivered to a subject animal including a human, method of delivery, number of inoculations, interval of inoculations, the type of subject animal and its condition.

"Vaccine" shall mean pharmaceutical formulations able to induce immunity.

"Immunity" shall mean a state of resistance of an subject animal including a human to a infecting organism or substance. It will be understood that infecting organism or substance is defined broadly and includes parasites, toxic substances, cancers and cells as well as bacteria and viruses. A therapeutically effective immunization course will produce the immune response.

"Immunization dose" shall mean the amount of antigen or immunogen needed to precipitate an immune response. This amount will vary with the presence and effectiveness of various adjuvants. This amount will vary with the animal and immunogen or antigen or adjuvant but will generally be between about 0.1 ug/ml or less to about 100 ug per inoculation. The immunization dose is easily determined by methods well known to those skilled in the art, such as by conducting statistically valid host animal immunization and challenge studies. See, for example, Manual of Clinical Immunology, H. R. Rose and H. Friedman, American Society for Microbiology, Washington, D.C. (1980). In some instances several immunization doses including booster doses will be administered to provide immunity, which collectively will be termed "Therapeutically Effective Immunization Course".

"Priming" shall mean the stimulation of a primary (as opposed to a secondary or later) response by an animal to an immunogen. The primary response is characterized by the manufacture by the animal of antibody to the immunogen, and ideally by the generation of a population of B-lymphocytes that respond to secondary or later immunogenic challenge—even absent adjuvant—with a rapid and substantive production of antibodies. Based upon such response 1, 2, 3 or more booster doses of immunogen absent adjuvant will generate a therapeutically effective immune response to the immunogen.

In particular embodiments of this invention the vesicles will have a net charge or be neutral. Charged vesicles are believed to display superior adjuvancy to neutral liposomes.

Salt forms of the derivatized sterols of the present invention are preferably used in the practice of the invention. In this aspect of the present invention, it is preferred that the proximal anchor (D) be charged and have a counterion (E). Generally any sterol which has been modified by the attachment of a charged group at the proximal (D) may be used in this aspect of the present invention.

In this immunization/adjuvant aspect of the present invention, it is preferred that the modifying moiety (D) be a carbonate. Thus, organic acids may be used to form the derivatized sterols of this immunization aspect of the present invention. Organic acids which may be used to derivatize the sterols include but are not limited to the carboxylic acids, dicarboxylic acids, polycarboxylic acids. In fact, preferred carboxylic acids are the hydroxy acids, amino acids and polyamino acids, because these carboxylic acids may be used to produce storage stable linkages (amine and ether linkages) at position (B) of the derivatized sterol.

Because the salt forms increase the water solubility of organic acids, a number of organic acids may be used to derivatize the sterols; however an advantage may be obtained if the organic acid moiety itself is water soluble. A further advantage is gained if the organic acid contains at least one additional reactive group which will form a storage stable linkage (B) of the derivatized sterol.

The derivatized sterols of the present invention advantageously form vesicles when added to an aqueous material. This can conveniently be performed at 20°–25° C. (room temperature) and atmospheric pressure. Agitation accelerates the process of vesicle formation and is preformed by such methods as vortexing, sonication or other methods well known in the art. If desired the resulting liposomes may be filtered or sized such as by passing through a filter stack such as a 0.4 or 0.2 um filter (Nuclepore, Pleasanton, CA). Typically better adjuvant response is observed with greater amounts of lipid. Immunogens which partition into the liposome lamellae such as melanoma antigen may yield an insufficient immunogenic response without repeated inoculations and additional immuno stimulator. Without being bound by any particular theory it is believed that this partitioning results in the limitation of exposure of epitopes externally to the adjuvant liposomes. Immunogens may be modified by a number of methods well known in the art such as by amino acid addition or subtraction or conjugation with other moieties.

In certain cases, the derivatized sterols of the present invention do not form liposomes. In certain of these cases an additional liposome forming lipid may be added to the steroidal component to promote the formation of liposomes.

A preferred class of lipids for forming vesicles of the present invention are those of dimyristoylphosphatidylcholine and derivatized sterol ("DMPC/derivatized sterol") in combination with an adjuvant inducing amount of a derivatized sterol of the present invention. DMPC/derivatized sterol forms the required multilamellar liposomes over a wide range of proportions from about 100:1 (molar) to about 20:80. More preferred is about 70:30 to about 30:70, and yet further preferred is about 70:30. Generally, the derivatized sterol is included in an amount of at least about 0.1 mole percent. Additionally other lipids may be admixed with DMPC/derivatized sterol, such as dimyristoyl phosphatidylglycerol, dicetyl phosphate, phosphatidic acid, phosphatidylethanolamine, phosphatidylcholine and cholesterol hemisuccinate ("CHS"), such as those with sodium ("CHSsodium") or tris(hydroxymethyl) aminomethane ("CHStris") as the counter ion.

Aluminum compounds, which may be added to the derivatized sterols of the present invention include adjuvants well known in the art, and include aluminum hydroxide, aluminum phosphate, aluminum oxide or aluminum sulfate and will be termed collectively aluminum adjuvants. By way of example, aluminum hydroxide is widely used in diphtheria and tetanus toxoid vaccines as well as in veterinary applications. Aluminum hydroxide powder spontaneously forms a gel upon hydration. To prepare a vaccine containing aluminum hydroxide, commonly immunogen in aqueous buffer is added to the preformed gel. Such vaccines are referred to as being aluminum-adsorbed.

DMPC/derivatized sterol multilamellar liposomes of the SPLV process are preferred but any other type of liposome may be used. The SPLV process generally involves rotoevaporation of lipids in solvent in a round bottom flask to form a thin film. The lipid film is then dispersed in a non-water miscible solvent such as ether or methylene chloride to which the aqueous solute (containing immunogen) is then added. The mixture is then sonicated while being dried by a stream of nitrogen gas which drives off the organic solvent. The resultant vesicle paste is resuspended in aqueous buffer. U.S. Pat. No. 4,522,803 to Lenk, et al. further describes this process and is incorporated herein by reference. If desired the resulting vesicles may be filtered or sized such as by passing through a filter stack such as a 0.4 or 0.2 um filter (Nuclepore, Pleasanton, CA).

The vesicles are conveniently administered in aqueous material. The volume of aqueous material will vary with the particular liposome to be administered and is not critical. Generally about 0.5 ml is a convenient liposome dosage volume. Typically better adjuvant response is observed with greater amounts of lipid.

Suitable aqueous material for either sterol or DMPC/derivatized sterol containing liposomes is saline solution, bovine serum albumen or other well known aqueous pharmaceutical diluents.

The vesicles of the present invention formed from an adjuvant inducing amount of a derivatized sterol are conveniently associated with an immunogenic amount of antigen or immunogen. This association is engendered by mixing, adsorption, encapsulation, co-formation or other methods well known in the art.

Aluminum adjuvants are used in forms and proportions well known to those skilled in the art. Commercial preparations of aluminum hydroxide gel containing vaccines such as tetanus toxoids range from about 0.2 to about 1 mg of aluminum/ml. The safe upper range is far higher—for humans vaccines with as much as 15 mg or more of aluminum hydroxide per dose are known with no limit for veterinary applications.

Vaccines are conveniently administered in a dosage form. A "dosage form" will be understood to mean any pharmaceutically form of administering a vaccine including subcutaneous, oral, intramuscular, and ocular administration and utilizing vaccines in live, attenuated or synthetic or partial forms along with adjuvants and optionally immunomodulators such as cytokines, for example rIL-2. The combinations of the foregoing elements are prepared so that the dosage form is adapted to produce an immune response in the subject animal including a human as easily and effectively as possible.

The dosage forms including liposomal dosage forms resulting from the method of the present invention can be used therapeutically in mammals, including man, in the treatment of infections or conditions which require the delivery of immunogen in its bioactive form. Such conditions include, but are not limited to, disease states such as those that can be treated with vaccines. Extracorporeal treatment of immunoresponsive tissues is also contemplated.

Dosage forms also include micelle forms of the adjuvant as well as adjuvant incorporated into gel such as aluminum gels, liquid crystals, powders, precipitates and solutions. In particular embodiments the dosage form can be a unit dosage form configured and adapted to a single administration.

The mode of administration of the dosage form may determine the sites and cells in the organism to which the dosage form will be delivered. The dosage forms including liposomal dosage forms of the present invention can be administered alone but will generally be administered in admixture with a pharmaceutical carrier selected with regard to the intended route of administration and standard pharmaceutical practice. The dosage forms may be injected parenterally, for example, intra-arterially or intravenously. The dosage forms may also be administered via oral, subcutaneous, or intramuscular routes. For parenteral administration, they can be used, for example, in the form of a sterile aqueous solution which may contain other solutes, for example, enough salts or glucose to make the solution isotonic. Other uses, depending upon the particular properties of the preparation, may be envisioned by those skilled in the art.

For administration to humans in the preventive or curative treatment of disease states responding to vaccine therapy, the prescribing physician will ultimately determine the appropriate therapeutically effective dosage for a given human subject, and this can be expected to vary according to the age, weight, and response of the individual as well as the nature and severity of the patient's disease. The dosage of the drug in liposomal dosage form will generally be about that or less than that employed for the free drug. In some cases, however, it may be necessary to administer dosages outside these limits.

The following examples are provided for purposes of illustration only and are not to be viewed as a limitation of the scope of the invention.

EXAMPLE 1

Synthesis of Cholesteryl-2-hydroxy-3-trimethylammonium-propylether

The alkoxide of cholesterol is produced by the reaction of sodium with cholesterol (molar ratio 1:1 in THF). After formulation, the alkoxide is reacted with 4-bromobutyrate, producing the ethyl ester of 4-butanoate by $SN_2$ nucleophilic displacement. The reaction, which produces substantial quantities of $E_2$ elimination product, may be improved by utilizing phase transfer catalysis or alternatively, by removing the ketone functionality of the ethyl ester as a ketal. The alkoxide is reacted with a molecule, for example, 2-(2-bromoethyl)-1,3-dioxane and the blocking acetal is removed with mild acid hydrolysis. Oxidation of the resulting aldehyde with manganese dioxide or oxygen produces the carboxylic acid. A second possible reagent for the ether synthesis is the epoxide glycidyltrimethylammonium chloride, which when reacted with the alkoxide of cholesterol produces the positively charged cholesteryl-2-hydroxy-3-trimethylammoniumpropyl ether. Upon heating the olefin would be produced.

EXAMPLE 2

Synthesis of Derivatized Sterol Having Amine Linkage (B)

The secondary amine may be conveniently synthesized by reductive alkylation. A keto steroid (at the 3 position) such as cholesterone or testosterone is condensed with the amine of a number of compounds, for example 4-aminobutyric acid which, after dehydration produces the Schiff's base at the 3 position. The resulting imine may be dehydrated with sodium borohydride or cyanoborohydride. The resulting product is the carboxylic acid cholesteryl 3-propanoic acid amine. The amine may be further alkylated with iodomethane or other alkylating agent to produce the tertiary amine or the quaternary ammonium salt at the 3 position of the sterol. This a very general reaction sequence and will yield numerous amino linked derivatized sterols in high yield.

EXAMPLE 3

Synthesis of Derivatized Sterols Having Sulfide Linkage (B)

The sulfide linkage at position 3 of the core molecule (A) is formed by nucleophilic substitution with a mercaptide. The 3 hydroxy position of cholesterol is tosylated (tosyl chloride/pyridine). The 3-0-tosyl group is then reacted with with the salt of a mercaptan, for example, 4-mercaptobutanoic acid (or the protected ester, thereof) to yield the sulfide of cholesteryl and and butanoic acid. To improve the yield of this reaction, phase transfer catalysis may be employed.

Grignard reagents could also be employed to provide the thio ethers. Reaction of cholesterol disulfide with magnesium 2(2-bromoethyl)-1,3-dioxolane yields the sulfide of cholesterol and the dioxolane. Mild acid hydrolysis and mild oxidation (oxygen) of the resulting aldehyde would give the carboxylic acid cholesteryl 3-propanoic acid sulfide.

EXAMPLE 4

Synthesis of Derivatized Sterols Having Alkyl Linkage (B)

Alkylation of cholesterol and other core molecules (A) of the present invention may be performed in a wide variety of ways. A number of positions other than the 3 position of cholesterol may be alkylated readily.

Grignard reagents react with ketosteroids to alkylate at the 3 position. Thus the reaction of the ketosteroid cholesterone or testosterone with magnesium 2(2-bromoethyl)-1,3-dioxolane will produce the alkyl derivative at the 3 position. Another possible alkylation is the reaction product of a magnesium bromide or lithium derivative of cholesteryl and an epoxide such as glycidotrimethyl ammonium chloride to produce the positively charged alkyl derivative of cholesterol B-hydroxy propyltrimethylammonium.

Another alkylation reaction is the reformatsky reaction with ethyl bromoacetate and cholesterone to product ethyl-3-cholesteryl acetate ester. Acid hydrolysis yields 3-cholesteryl acetic acid.

EXAMPLE 5

Synthesis of Derivatized Sterols Having Amide Linkage (B)

Cholesteryl amides may be made very simply by reacting an anhydride with the cholestyramine to give the amide linked product. Numerous anhydrides may be reacted with the amine including succinimic anhydride to produce the amide linked cholesterylhydrogensuccinimide. A large number of substitutions may be made using this general procedure.

EXAMPLE 6

Preparation of Adjuvant Liposomes with Antigen

About 50 mg of any of the derivatized sterols from Examples 1-5 (powdered) are placed into a 15 ml test tube. 100 ul of bromelain fragment of HA in aqueous buffer is added (about 650 ug HAB, 0.01M phosphate buffered saline in 0.9%NaCl). The mixture is intermittently vortexed over a 2-hour period at 22.5° C.+2.5° C. and left until no large clumps are visible. The resultant liposomes are washed 3 times in 10 ml of aqueous buffer solution being separated each time by 15 minutes of centrifugation (10,000 rpm, J-20 rotor (Beckman, Palo Alto, CA)). The final pellet is brought to 4.0 ml in buffer and sealed in an amber vial under nitrogen.

EXAMPLE 7

Preparation of Adjuvant Liposomes with Antigen

Approximately 500 mg of any of the derivatives from Examples 1 through 5 (powdered) are placed into a 15 ml test tube. 1 ml of HA in aqueous buffer is added (approximately 300 ug HA, 0.01M phosphate buffered saline in 0.9%NaCl) The mixture is intermittently vortexed over a 2 hour period at 22.5° C.+2.5° C. The resultant vesicles are washed 3 times in about 10 ml of aqueous buffer solution being separated each time by 15 minutes of centrifugation (10,000 rpm, J-20 rotor (Beckman, Palo Alto, CA)). The final pellet is brought to about 4.0 ml in buffer and sealed in an amber vial under nitrogen.

EXAMPLE 8

Preparation of Adjuvant Liposomes with Antigen

Approximately 500 mg of any of the derivatives from Examples 1 through 5 (powdered) are placed into a 15 ml test tube. 1 ml of bromelain fragment of HA in aqueous buffer is added (approximately 650–675 ug HAB, 0.01M phosphate buffered saline in 0.9%NaCl). The mixture is intermittently vortexed over a 2-hour period at 22.5° C.+2.5° C. The resultant vesicles are washed 3 times in 10 ml of aqueous buffer solution being separated each time by 15 minutes of centrifugation (10,000rpm, J-20 rotor) The final pellet is brought to 4.0 ml in buffer and sealed in an amber vial under nitrogen.

EXAMPLE 9

Preparation of Adjuvant Liposomes with Antigen

Approximately 500 mg of any of the derivatives from Examples 1 through 5 (powdered) are placed into a 15 ml test tube. About 2 ml of bromelain fragment of HA in aqueous buffer is added (1,100 ug HAB, 0.9%NaCl). The mixture is intermittently vortexed over a 2-hour period at 22.5° C.+2.5° C. The resultant vesicles are washed 3 times in 10 ml of 0.9%NaCl solution being separated each time by 15 minutes of centrifugation (10,000 rpm, J-20 rotor). The final pellet is brought to 4.0 ml in buffer and sealed in an amber vial under nitrogen.

EXAMPLE 10

Preparation of Gel Admixed with Liposomes

Aluminum hydroxide gel, 2% (Alhydrogel TM; Connaught Laboratories, Inc., Swiftwater, PA) containing 7.29 mg/ml aluminum is used in conjunction with 1.02 ml of the liposomes of this invention prepared as in Example 9. The liposomes are admixed with 0.67 ml aluminum hydroxide gel and 5.31 ml of saline. The final aluminum concentration is 0.7 mg/ml and the HAB concentration is 10 ug/ml. The mixture is sealed in a glass vial with rubber stopper and crimp seal.

EXAMPLE 11

Preparation of Lipsosomes from Tris-Salt Derivatized Sterols

About 50 mg. of any of the derivatized sterols from Examples 1 through 5 containing a carboxylate as proximal anchor (D) and TRIS as the counterion is added to approximately a 1 ml. solution of arsenazo III (4.5 mM final concentration) in 0.01 M TRIS-HCl (pH approximately 7.3), 0.15M NaCl. A milky suspension of MLV's is formed by mechanical shaking. In certain cases, depending upon the derivatized sterol used, the suspension of MLV's may be mixed vortically with glass The MLV's are pelleted by centrifugation at 10,000×g for 15 minutes, and the resulting pellet is washed three times using 10 ml of 0.01 M TRIS-HCl (pH approximately 7.3). The resulting pellet, which is red in color, indicates entrapment of the arsenazo III. Liposomes prepared from other derivatized sterols wherein the salt may be prepared as described above, or by following the procedure of Janoff, et al. set forth in U.S. Pat. No. 4,721,612, which is incorporated by reference herein.

EXAMPLE 12

Entrapment of Various Agents in Vesicles Prepared from Derivatized Sterols of the Present Invention In general, the procedure of Janoff, et al., U.S. Pat. No. 4,721,612 is followed with obvious modification. In addition to numerous bioactive agents, inulin, chromium, growth hormone, insulin, tylosin, and diazepam may be entrapped in liposomes prepared from the derivatized sterols of the present invention. Therapeutic methodology in utilizing bioactive agents entrapped in liposomes closely adheres to the teachings of the art.

It will be understood by those skilled in the art that the foregoing description and examples are illustrative of practicing the present invention, but are in no way limiting. Variations of the detail presented herein may be made without departing from the spirit and scope of the present invention.

We claim:

1. Storage stable steroidal vesicles, the vesicles being storage stable for a period of at least one year, comprising completely closed bilayers formed from a derivatized sterol of the general structure:

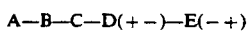

wherein:
- A is a core molecule selected from the group consisting of sterols, steroids, bile acids and intermediates of sterol metabolism;
- B is a chemical bridge, between the 3 position of the core molecule (A) and anchor molecule (C), selected from the group consisting of ether, amine, alkylene and amide linkages;
- C is an anchor molecule selected from the group consisting of:
  - C2 to C8 linear alkyl groups;
  - branched-chain alkyl groups comprising C2 to C8 linear alkyl chain and one or more methyl, ethyl, propyl or isopropyl side groups linked to methylene groups within the alkyl chain;
  - carbocyclic structures selected from the group consisting of unsubstituted and substituted cyclopentyl, cyclohexyl, phenyl and benzyl groups;
  - heterocyclic structures selected from the group consisting of tetrazoles, triazoles, pyrroles, pyrrolidines, pyrrolidones, and pyridines; and
  - sugars selected from the group consisting of unsubstituted and substituted pentose and hexose sugars;
- D is a charged hydrophilic group selected from the group consisting of carboxylates, carbonates, phosphates, sulfonates, borates, sulfates, protonated amines, quarternary amines, imidazoles, sulfonium groups, phosphonium groups, pyridinium groups, pyrroles, tetrazoles and triazoles; and
- E is a charged counterion to D.

2. The vesicles according to claim 1 wherein said charged counterion E is selected from the group consisting of acetates, sulfates, phosphates, arsenates, borates, nitrates, chlorates, metal ions, amines, imidazoles, pyridinium groups, sulfonium groups and phosphonium groups.

3. The vesicles according to claim 1 wherein said charged counterion E is selected from the group consisting of amino acids, peptides, peptide fragments, proteins, nucleotides, nucleosides, nucleoproteins, glycoproteins, oligonucleotides, polynucleotides, ethylenediaminetetracetic acid, tris(hydroxymethyl)aminomethane, choline and miconazole.

4. The vesicles according to claim 1 further comprising a bioactive agent.

5. The vesicles according to claim 1 wherein the vesicles are multilameller vesicles.

6. The vesicles according to claim 1 wherein the vesicles are unilamellar vesicles.

7. The vesicles according to claim 1 wherein D is a carbonate or carboxylate and E is a positively charged tris(hydroxymethyl)aminomethane.

8. The vesicles according to claim 1 wherein said core molecule (A) is selected from the group consisting of aldosterone, androsterone, testosterone, estrogen, ergocalciferol, ergosterol, estradiol-17alpha, estradiol-17beta, cholesterol, cholic acid, corticosterone, estriol, lanosterol, lithocholic acid, progesterone, cholecalciferol, cortisol, cortisone, cortisone acetate, cortisol acetate, deoxycorticosterone, estrone, and phytosterols.

9. The vesicles according to claim 8 wherein said core molecule (A) is cholesterol.

10. A method for administering a bioactive agent in vivo to a host, said method comprising administering the agent entrapped in storage stable steroidal vesicles, the vesicles being storage stable for a period of at least one year, said vesicles comprising completely closed bilayers formed from a derivatized sterol of the general structure:

wherein:
- A is a core molecule selected from the group consisting of sterols, steroids, bile acids and intermediates of sterol metabolism;
- B is a chemical bridge, between the 3 position of the core molecule (A) and anchor molecule (C), selected from the group consisting of ether, amine, alkylene and amide linkages;
- C is an anchor molecule selected from the group consisting of:
  - C2 to C8 linear alkyl groups;
  - branched-chain alkyl groups comprising a C2 to C8 linear alkyl chain and one or more methyl, ethyl, propyl or isopropyl side groups linked to methylene groups within the alkyl chain;
  - carbocyclic structures selected from the group consisting of unsubstituted and substituted cyclopentyl, cyclohexyl, phenyl and benzyl groups;
  - heterocyclic structures selected from the group consisting of tetrazoles, triazoles, pyrroles, pyrrolidines, pyrrolidones, and pyridines; and
  - sugars selected from the group consisting of unsubstituted and substituted pentose and hexose sugars;
- D is a charged hydrophilic group selected from the group consisting of carboxylates, carbonates, phosphates, sulfonates, borates, sulfates, protonated amines, quarternary amines, imidazoles, sulfonium groups, phosphonium groups, pyridinium groups, pyrroles, tetrazoles and triazoles; and
- E is charged counterion to D.

11. The method according to claim 10 wherein said charged counterion E is selected from the group consisting of acetates, sulfates, phosphates, arsenates, borates, nitrates, chlorates, metal ions, amines, imidazoles, pyridinium groups, sulfonium groups and phosphonium groups.

12. The method according to claim 10 wherein said charged counterion E is selected from the group consisting of amino acids, peptides, peptide fragments, proteins, nucleotides, nucleosides, nucleoproteins, glycoproteins, oligonucleotides, polynucleotides, ethylenediaminetetracetic acid, tris(hydroxymethyl)aminomethane, choline and miconazole.

13. The method according to claim 10 wherein said vesicles are multilamellar vesicles.

14. The method according to claim 10 wherein said vesicles are unilamellar vesicles.

15. The method according to claim 10 wherein D is a carbonate or carboxylate and E is a positively charged tris(hydroxymethyl)aminomethane.

16. The method according to claim 10 wherein said core molecule (A) is selected from the group consisting of aldosterone, androsterone, testosterone, estrogen, ergocalciferol, ergosterol, estradiol-17alpha, estradiol-17beta, cholesterol, cholic acid, corticosterone, estriol, lanosterol, lithocholic acid, progesterone, cholecalciferol, cortisol, cortisone, cortisone acetate, cortisol acetate, deoxycorticosterone, estrone, and phytosterols.

17. The method according to claim 16 wherein said core molecule (A) is cholesterol.

18. An immunizing dosage form comprising an immunization dose of storage stable steroidal vesicles and an antigen, the vesicles being storage stable for a period of at least one year, said vesicles comprising completely closed bilayers formed from a derivatized sterol of the general structure:

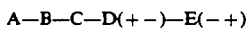

A—B—C—D(+ —)—E(— +)

wherein:
A is a core molecule selected from the group consisting of sterols, steroids, bile acids and intermediates of sterol metabolism;
B is a chemical bridge, between the 3 position of the core molecule (A) and anchor molecule (C), selected from the group consisting of ether, amine, alkylene and amide linkages;
C is an anchor molecule selected from the group consisting of:
C2 to C8 linear alkyl groups;
branched-chain alkyl groups comprising a C2 to C8 linear alkyl chain and one or more methyl, ethyl, propyl or isopropyl side groups linked to methylene groups within the alkyl chain;
carbocyclic structures selected from the group consisting of unsubstituted and substituted cyclopentyl, cyclohexyl, phenyl and benzyl groups;
heterocyclic structures selected from the group consisting of tetrazoles, triazoles, pyrroles, pyrrolidines, pyrrolidones, and pyridines; and
sugars selected from the group consisting of unsubstituted and substituted pentose and hexose sugars;

D is a charged hydrophilic group selected from the group consisting of carboxylates, carbonates, phosphates, sulfonates, borates, sulfates, protonated amines, quarternary amines, imidazoles, sulfonium groups, phosphonium groups, pyridinium groups, pyrroles, tetrazoles and triazoles; and
E is a charged counterion to D.

19. The dosage form according to claim 18 wherein said charged counterion E is selected from the group consisting of acetates, sulfates, phosphates, arsenates, borates, nitrates, chlorates, metal ions, amines, imidazoles, pyridinium groups, sulfonium groups and phosphonium groups.

20. The dosage form according to claim 18 wherein said charged counterion E is selected from the group consisting of amino acids, peptides, peptide fragments, proteins, nucleotides, nucleosides, nucleoproteins, glycoproteins, oligonucleotides, polynucleotides, ethylenediamintetracetic acid, tris(hydroxymethyl)aminomethane, choline and miconazole.

21. The dosage form according to claim 18 wherein said antigen is selected from the group consisting of proteins, peptides, polysaccharides, nucleic acids, lipids, glycolipids, lipoproteins, lipopolysaccharides, viral fractions, tissue fractions and cellular fractions.

22. The dosage form according to claim 21 wherein said antigen is selected from the group consisting of influenza virus fractions, parainfluenza 3, malaria sporozoite fractions, hepatitus A virus fractions, hepatitis B virus fractions, hepatitis non-A/non-B virus fractions, meningococcus fractions, HIV fractions and melanoma cell fractions.

23. The dosage form according to claim 22 wherein said influenza fractions are selected from the group consisting of hemagglutinin, neuraminidase, and fragments thereof.

24. The dosage form according to claim 23 wherein said antigen is the bromelain fragment of the hemagglutinin fraction of influenza virus.

25. The dosage form according to claim 18 wherein said antigen is entrapped in the vesicles.

26. The dosage form according to claim 18 wherein said vesicles are multilamellar.

27. The dosage form according to claim 26 wherein said vesicles are at least about 1 micron in diameter.

28. The dosage form according to claim 18 wherein said vesicle comprises an adjuvant inducing amount of said derivatized sterol in combination with a liposome forming lipid.

29. The dosage form according to claim 28 wherein said liposome forming lipid is dimyristoylphosphatidylcholine.

30. The dosage form according to claim 18 further comprising an immunomodulator.

31. The dosage form according to claim 30 wherein said immunomodulator is a cytokine.

* * * * *